(12) United States Patent
Carver et al.

(10) Patent No.: US 6,514,763 B2
(45) Date of Patent: Feb. 4, 2003

(54) HEMATOLOGY BLOOD CONTROL AND METHOD FOR PREPARATION OF SAME

(75) Inventors: Franklin J. Carver, Marco Island, FL (US); James D. Lapicola, Pleasant Hill, CA (US)

(73) Assignee: Hematronix, Inc., Plano, TX (US)

( * ) Notice: Subject to any disclaimer, the term of this patent is extended or adjusted under 35 U.S.C. 154(b) by 0 days.

(21) Appl. No.: 09/816,911

(22) Filed: Mar. 23, 2001

(65) Prior Publication Data

US 2001/0046708 A1 Nov. 29, 2001

Related U.S. Application Data

(60) Provisional application No. 60/200,451, filed on Apr. 28, 2000.

(51) Int. Cl.⁷ .............................................. G01N 31/00
(52) U.S. Cl. ............................... 436/10; 436/8; 436/17; 436/63; 252/408.1
(58) Field of Search ............................... 436/8, 10, 17, 436/18, 63, 174, 176; 252/408.1

(56) References Cited

U.S. PATENT DOCUMENTS

| | | | |
|---|---|---|---|
| 2,656,508 A | 10/1953 | Coulter | 324/71.1 |
| 4,099,917 A | 7/1978 | Kim | 436/10 |
| 4,286,963 A | 9/1981 | Ledis et al. | 436/63 |
| 4,751,179 A | 6/1988 | Ledis et al. | 435/34 |
| 5,155,044 A | * 10/1992 | Ledis et al. | 436/17 |
| 5,188,935 A | * 2/1993 | Leif et al. | 435/7.24 |
| 5,677,145 A | 10/1997 | Ryan | 436/10 |
| 5,731,205 A | 3/1998 | Ryan | 436/10 |
| 5,731,206 A | 3/1998 | Ledis et al. | 436/17 |
| 5,858,790 A | 1/1999 | Kim et al. | 436/16 |
| 6,146,901 A | 11/2000 | Carver et al. | 436/174 |

FOREIGN PATENT DOCUMENTS

WO     WO 96/34283     10/1996

* cited by examiner

*Primary Examiner*—Maureen M. Wallenhorst
(74) *Attorney, Agent, or Firm*—Stinson Morrison Hecker LLP

(57) ABSTRACT

The control of the present invention involves a gentle chemical removal of red cells, leaving an intact white cell preparation. The preservation steps, namely the use of cross-linking agents as aldehydes, involve a step-wise process starting with very low concentrations of a cross-linking agent. The fixation part of the process outlined in this disclosure has also been applied to non-mammalian blood cells and therefor would appear to be a universal procedure for preparing all types of vertebrate blood cells.

15 Claims, No Drawings

HEMATOLOGY BLOOD CONTROL AND METHOD FOR PREPARATION OF SAME

CROSS-REFERENCE TO RELATED APPLICATION

Pursuant to 35 U.S.C. §119(e), this application claims the benefit of U.S. provisional application Ser. No. 60/200,451, filed Apr. 28, 2000, entitled Hematology Blood Control and Method for Preparation of Same, the entirety of the disclosure of which is hereby specifically incorporated by reference.

FIELD OF THE INVENTION

The present invention relates to a hematology blood control and, more particularly, to a hematology control made from human leukocytes and a method for the preparation of the control.

BACKGROUND OF THE INVENTION

Instruments for the analysis of blood components and chemistry have been used for many years. The accuracy and sensitivity of these hematology instruments have steadily advanced. The early forms of hematology instrumentation have evolved to relatively complex machines that analyze the discreet components of blood based upon the intricate and subtle characteristics of its components.

The most recent iteration in automated hematology instrumentation has been the multi-part analysis of human white cells, in addition to the detection of red blood cells and platelets. The white cell populations typically include lymphocytes, monocytes, neutrophils, basophils, and eosinophils. The methods for blood cell analysis involve the electrical and optical properties of each type of blood cell. The Beckman-Coulter™ five-part white cell analysis instrument uses three different types of technologies, which include electrical impedance, a DC mathematical manipulation called conductance, using a low voltage DC (direct current) measurement, Rf (radio frequency modulation), and laser technology which includes light scatter and light absorption. The Rf measurement is typically used with the DC low frequency measurement to create a parameter called opacity which is a calculation of Rf divided by DC. Instruments by other manufacturers, such as Abbott Diagnostics™, Technicon™, and TOA™, use a combination of electrical impedance, DC conductance and/or laser technology, Rf, depolarized 90° angle light scatter, and/or light absorption. Although the basic types of electronic technology may appear the same, each manufacturer has a unique implementation for the instrument hardware and software that is required to analyze blood cells. The individual implementations of this technology by the various manufacturers have resulted in a wide array of reagents and methodology for each specific instrument of each manufacturer, thereby increasing the complexity and expense of their use. There is no one reagent or methodology that can be used with a plurality of instruments.

In order to ensure that a hematology instrument is working properly, it has been mandated by governments that there be a method to verify the integrity of the instrument using a blood control. The control should contain particles that represent all of the cellular elements of fresh blood, as well as a liquid component that serves as a suspending media similar to the function of human plasma. This synthetic plasma usually contains components that are the same as or function the same as native plasma. The components of synthetic plasma include inorganic salts, organic and/or inorganic buffers, and a viscous material for maintaining homeostasis similar to the plasma proteins. The manufacturer of a control provides all of the critical values such as cell count, cell size, and cell type. The control material should have sufficient shelf life to be used for days, weeks, or months to ensure the consistency of instrument performance over time.

The method for preparing a hematology control is dependent on the hardware and software design of the specific instrument in which the control is to be used, as well as the requirements for extended shelf life. Particles in blood control products that work like human white cells, red blood cells, or platelets on a Coulter™ type instrument may not work effectively on other instruments, such as instruments manufactured by Abbott Laboratories™, Technicon™, or TOA™ instruments.

Moreover, because these particles are usually modified from various types of blood cells, they do not behave like living native fresh blood cells. Consequently, human white cells fixed with a cross-linking agent like glutaraldehyde may behave like a neutrophil on an Abbott™ instrument, but behave like cellular debris on a Coulter™ instrument. Specially treated and cross-linked red blood cells from non-mammalian vertebrates may look like mononuclear cells on one type of hematology instrument and look like lymphocytes on another.

SUMMARY OF THE INVENTION

It is therefore an object of the present invention to provide a method for preparing white blood cells from a vertebrate source for use in a hematology blood control product. The method provides sufficient flexibility to compensate for the different technologies employed by instrument manufacturers. Thus, it is an object of the present invention to customize a process using the described method, resulting in a hematology control unique to a hematology instrument specification.

It also is an object of the present invention to provide a method to prepare a hematology blood control from human white cells without the need for plasma cholesterol to maintain the electrical and/or optical characteristics of the cells.

It is a further object of the present invention to provide a hematology blood control that can be utilized on a plurality of instruments made by different manufacturers.

It is yet another object of the present invention to provide a hematology blood control that can be prepared easily and inexpensively.

To accomplish these and other related objectives, the control of the present invention is achieved using a gentle chemical removal of red cells, leaving an intact white cell preparation. The preservation steps, namely the use of cross-linking agents as aldehydes, involves a step-wise process starting with very low concentrations of a cross-linking agent. The fixation part of the process outlined in this disclosure has also been applied to non-mammalian blood cells and therefor would appear to be a universal procedure for preparing all types of vertebrate blood cells. The examples below include small as well as large volume processes. It has been found that the concentration and timing elements must be adjusted based on the volume of the reaction mixture. Thus, a final volume of 15 mL will require different proportions of elements and different timing steps compared to a 1 liter batch. For example, it is possible to perform a 15 second centrifugation with a 15 mL tube process but this 15 second step is essentially impossible with a 1 L bottle batch. The selective use of lytic agents and the unique fixation process eliminates the need for supportive reagents as cholesterol, which have been found to be necessary for the successful display of preserved human white cells.

DETAILED DESCRIPTION

The basic components for the preparation of the control of the present invention include the following:

A quantity of source leukocytes between 0–5 days old, preferably one day old, stored in a styrofoam or other insulated container with sufficient cold packs to insure the units are cool but not cold. Overnight storage at 4° C. will sufficiently alter the quality of the white cells or potentially require modifications in the processing of the blood.

A lytic agent including of any one or a combination of the following:
  an organic acid such as formic, acetic, and propionic acids. The preferred acid is propionic acid.
  a quantity of saponin in water. Suitable types of saponin include, but are not limited to, Sapindus and Quillaja. The preferred saponin is Sapindus.

A quench made with inorganic salts including one or a combination of the following:
  Carbonate buffered, similar to that used in certain commercial products, such as Hematronix, Inc Diff Pak™ containing sodium carbonate, sodium sulfate, and sodium chloride.
  Buffer free sodium sulfate and sodium chloride salts.
  Buffer free sodium sulfate only
  Buffer free sodium chloride only
  Sodium phosphate only
  Any of the above salt solutions with cross-linking agent.

A post-lytic hypotonic fixing reagent including one or more of the following:
  Low osmolarity salt, such as diluted M-Ringers, an α-naphtol based salt solution, or diluted mammalian balanced salt solution as Osmocel®.
  a low carbon number glycol, such as propylene glycol
  a cross-linking agent, such as an aldehyde like glutaraldehyde.

An additional post-lytic reagent including one or more of the following:
  a cross-linking agent, such as an aldehyde like glutaraldehyde.

The preferred method for achieving the control of the present invention includes the gentle removal of non-white cell components from commercially available Source Leukocytes and the gentle step-wise preservation of the remaining white cells. The gentle removal of non-white cell components (i.e. red blood cells) from Source Leukocytes requires a lytic agent which preferentially removes blood cells. The preferred lytic agent includes a specific type of saponin called Sapindus. Other agents, such as short chain fatty acids with or without saponin, are also effective. Optimization of the process with saponin rather than a short chain fatty acid showed better performance when comparing weak versus strong Coulter instrument reagents.

The time of Source Leukocyte exposure to lyse and the volume of lyse are directly related to the size (volume) of the prepared white cells. Increased lyse time destroys non-neutrophil particles (i.e. lymphocytes, monocytes, and eosinophils) faster than neutrophil particles. The red blood cell count in the Source Leukocyte material has some effect (slight increase in white cell volume with increased red cell count) on the quality of the preserved white cells when using low red cell count versus high red cell count in the Source Leukocyte units.

After lytic treatment of the Source Leukocytes, the remaining white cells are exposed to a hyperosmotic salt solution (i.e. quench) containing no fixative or a low to moderate concentration of fixative, in the range of 0.1% to 0.5%. The salt solution raises the ionic strength to normal or near normal concentration and it prevents protein agglutination and controls the cell size and laser light scatter. The low concentration of cross-linking agent in the quench or added soon after the quench, provides a mild stabilization of the protein moieties of the white cells.

The cells in lyse, quench, and glutaraldehyde are incubated for a short time, approximately one hour or less. Then the lytic/quench/fix solution is replaced with a hyposmotic solution containing a second round of low to moderate cross-linking agent, from about 0.5 to 10% glutaraldehyde, for 1–8 days at room temperature. It is preferable that the solution be kept at approximately 37° C. for a period of time, preferably 2 and one-half hours, to maintain long term stability of cellular characteristics as observed on a Coulter™ 5-part WBC analyzer. Incremental decreases in the salt concentration will increase the particle volume and decrease Coulter™ Scatter. Incremental increases in the salt concentration will decrease particle volume and increase Coulter™ Scatter. Adding a cross-linking agent after exposure to the hyposmotic salt solutions results in a slightly higher volume than adding directly to the hyposmotic salt solution. If a larger volume is required, adding the cross-linking agent to the hyposmotic solution will provide an incremental increase in volume.

A third fixation may be applied using moderate to high glutaraldehyde fixation, from about 1–20%. The fixative is typically added directly to the supernatant rather than washing the cells as part of the third (tertiary) fixation.

The general procedure for treating human white cells includes a very low concentration of fixative after red cell lysis. Successive fixations involve an increase in the concentration of cross-linking agent by geometric or preferred log concentrations. The successive fixation steps are performed to maintain the characteristics of non-treated white cells and to extend the stability of the treated white cells. For example, if the first fix is at 0.1% glutaraldehyde, the second fixation would be 1% and the third would be 10%. In concert with the progressive fixation steps, it has been found that elevated heating of the secondary fixed cells for the first 0.25–2 hours of exposure results in larger more stable particles. To provide added stability, a third fixation step is provided at a higher concentration of cross-linking agent than the first and second fixation steps.

Finally, the fixed white cells are washed in a hyposmotic solution then resuspended and stored in an hyposmotic or isosmotic solution for 1–30 days then added to preserved red blood cells in a synthetic plasma.

Decreasing the ionic strength from 60% Ringers to 20% Ringers will increase the volume depending on the strength of the cross-linking agent.

Some of the fixation steps, such as the first and third, are not required to obtain acceptable results, but do provide better quality and better long term stability. The gentle removal of non-white cell elements, the timing of the lysis, the use of lyse concentration and lyse volume, and the use of low to high concentrations of cross-linking agents during the process provide the desired stability and quality to be maintained in a commercial blood control red blood cell suspension.

Another agent important to the process is a low molecular weight glycol, such as propylene glycol, which has been found to selectively preserve white cells that have unique properties depending on the assay instrument. For example, propylene glycol was found to effect the display of particles in the monocyte region on the Coulter™ Model MAXM™ where the same preparation on the Abbott™ 3500™ did not display the particles in the monocyte region. If the propylene glycol was removed from the preparation of Source Leukocytes, there was no display of particles in the monocyte region on the Coulter™ instrument, but they were present with the Abbott™ instrument.

The preferred method for preparing a hematology control in accordance with the present invention includes the following:

The time of cell exposure to lyse is reduced by optimizing:
  the concentration of the lytic agent
  having the largest practical ratio of lyse to Source Leukocytes.
the cells were given a preliminary fix as quickly as possible (elevated heat) with the lowest concentration of cross-linking agent (e.g. 0.1% glutaraldehyde).
fixation with a low to moderate concentration of agent to provide moderate stability.
fixation with a moderate to high concentration of agent to provide long term stability.

EXAMPLES

The following represent materials and methods for preparing human white cells from human blood.

Materials

Source Leukocytes 1–3 days from collection at a blood bank with an RBC count of 0.5 to $7 \times 10^6/\mu L$ and a white cell count of from about 1 to $80 \times 10^3/\mu L$.

Reagent glutaraldehyde (25%). This glutaraldehyde concentration is a percentage of reagent glutaraldehyde. If a primary fixation requires a 1% concentration, it would be 1% of reagent glutaraldehyde. The true glutaraldehyde concentration would be 1% of 25 or 0.25% glutaraldehyde.

Reagent formaldehyde (37%) This formaldehyde concentration is a percentage of reagent formaldehyde. If a primary fixation requires a 1 % concentration, it would be 1 % of reagent formaldehyde. The true formaldehyde concentration would be 1% of 37 or 0.37% formaldehyde.

Reagent Acrolein; Sigma Part# A-2773

Reagent Saponin including the type Sapindus and the type Quillaja (Sigma) for the lysis of red cells.

Sapindus saponin, liquid (Dr. H Schmittman Guibii Type S-CN)

Sapindus saponin, powder (Dr. H Schmittman)

Quillaja saponin, powder Lot# 73H2605 (Sigma Chemicals)

Standard Saponin preparation:
  Reagent Saponin: chemical provided by the vendor.
  Stock Solution: Obtain a 25 mL sample of liquid Reagent Sapindus or a 25 g sample of powdered Sapindus or Quillaja saponin and dissolve into one liter of a 50% M-Ringers or 50% α-napthol-saline solution (ideally 50% α-napthol-saline solution; ref Cd108).
  Working Solution: Add stock solution to purified water prepared by reverse osmosis. The Working Solution is then used for treating the Source Leukocyte material. The final concentration of the working solution is 0.2 mL Reagent saponin/Liter of water to 1.625 mL Reagent Saponin/Liter of water. The powdered Quillaja has been found to have about a 30%–50% lesser potency when assays for liquid saponin are corrected for specific gravity. Powdered Sapindus is about >20% more potent than the liquid Sapindus.

Short chain fatty acids. Ideally the chain length is less than eight with a chain length of 5 preferred.

Quench; carbonate buffered

| Component | Amount | ± |
|---|---|---|
| Sodium Carbonate | 8.200 | |
| Sodium Chloride | 11.200 | |
| Sodium Sulfate | 31.300 | |
| pH | 11.050 | 0.100 |
| Conductivity | 54,250 | 250 |

Quench; no buffer

| Component | Amount | ± |
|---|---|---|
| Sodium Chloride | 8.0 | |
| Sodium Sulfate | 46.0 | |
| pH | 9.21 | 3.5–9.21 |
| Osmolarity | 970 | 800–1,200 |

Other formulas at a comparable Osmolarity:
  Sodium Chloride only
  Sodium Phosphate only.
  Sodium Sulfate only
  α-napthol only Cross-linking agent, (preferred reagent is glutaraldehyde; may also use Acrolein or its derivatives).

Saponin of the type Sapindus. Stock solution 25 mL liquid concentrate (specific gravity=~1.1) in a 50% solution of Modified Amphibian Ringers.

Lysing Solution consists of 0.030–0.60 L of the saponin stock solution and make up to the 1 liter volume in reverse osmosis or distilled treated water. Actual concentration based on the potency of each lot of saponin. Final concentration of 0.24 to 1.8 g/L.

Modified Amphibian Ringers (M-Ringers)

| Component | Amount | ± |
|---|---|---|
| Sodium chloride | 6.500 | |
| Potassium chloride | 0.140 | |
| MOPS | 2.090 | |
| P150 | 0.200 | |
| Sodium hydroxide | 0.225 | |
| pH | 7.2 | |
| Osmolarity | 230 | 5 |

α-napthol-saline
Preserved human red blood cells in a synthetic plasma media.
1 L centrifuge bottles.
50 mL centrifuge tubes.

The general process of this invention involves the lysis of red blood cells and the retention of white blood cells by using cell surface disruption. The process utilizes a low concentration of lytic agent(s) for a relatively short period of time. The agents include weak organic acids and/or saponin. The lysed cells are removed by centrifugation and resuspended in a weak to moderate concentration of cross-linking agent. Additional agents may be used to control the white cell modification process and include propylene glycol.

Example 1

Propionic acid/Saponin lyse system, carbonate buffered quench, with a propylene glycol based aldehyde fix.

Resuspended the Source Leukocyte cells contained in the transfer bags supplied by the blood bank and pipet 0.5–2 parts (preferably 1 mL) from the transfusion bag into a 15 mL centrifuge tube.

Add 6–12 parts (preferably 8 mL) of a commercial lytic solution (Hematronix™ lyse with propionic acid and saponin or Coulter™ lyse with formic acid and saponin).

After 15–30 seconds (preferably 15 seconds), add 1–2 parts (preferably 1 mL) of a carbonate buffered quench. Desirable results may not be obtained by using 0.5 parts quench.

After exposure to the quench for 5–15 seconds (preferably 10 seconds), centrifuge at 3,000 RPM for 0.5–3 minutes (preferably 1 minute).

Aspirate the supernatant and replace with a 0.1 to 5% glutaraldehyde solution (preferably 1 %) containing 30–80% Ringers (preferably 60%) with 5–20% propylene glycol (by volume of Ringers) (preferably 10% propylene glycol) or without propylene glycol.

NOTE: Experiments Cd001 through Cd004 demonstrate that one can obtain qualitatively different populations with and without propylene glycol.

Fix for 4 or more hours at room temperature.

An additional fixation may be applied as 10% by volume of reagent glutaraldehyde or formaldehyde to improve cell stability (Cd068; book#18) This is a direct addition of cross-linking agent. Experiments indicate that removal of supernatant and replacement with a salt-free fixative will cause a significant change (i.e. drop in volume) of all preserved human white cells.

Wash the cells 1–3 times with M-Ringers. Number of washes depends on the concentration of the residual material, i.e., glutaraldehyde.

Example 2

Same as Example 1, but with propionic acid only lyse system. Reaction is in a 50 mL tube.

Resuspend the Source Leukocyte cells contained in the transfer bags supplied by the blood bank and pipet 0.5–2 parts (preferably 5 mL) from the transfusion bag into a 50 mL centrifuge tube.

Add 6–12 parts (preferably 8 parts or 40 mL) of 0.3 to 0.6% propionic acid lyse (preferably 0.6%).

After 2–6 minutes (preferably 4 minutes), add 1–3 parts (preferably 1 mL) of a carbonate buffered quench.

After exposure to the quench for 1–6 minutes (preferably 1 minute), centrifuge at 3,000 RPM for 0.5–3 minutes (preferably 1 minute).

Aspirate the supernatant and replace with a 0.1 to 5% glutaraldehyde solution (preferably 1 %) containing 30–80% Ringers (preferably 60%) with 5–20% propylene glycol (by volume of Ringers) (preferably 10% propylene glycol) or without propylene glycol. One can obtain qualitatively different populations with and without propylene glycol. The salt concentration in the fix solution is inversely related to the size (volume) of the particles within the 30–80% range of M-Ri.

Fix for 4 or more hours at room temperature.

An additional fixation may be applied as 10% by volume of reagent glutaraldehyde or formaldehyde to improve cell stability. This is a direct addition of cross-linking agent. Experiments indicate that removal of the supernatant and replacement with salt-free fixative will cause a significant change (i.e. drop in volume) of all preserved human white cells.

Wash the cells 1–3 times with M-Ringers. Number of washes depends on the concentration of the residual material, i.e. glutaraldehyde.

Example 3

Same as Example 2, but process 250 mL in a 1 L bottle.

Resuspend the Source Leukocyte cells contained in the transfer bags supplied by the blood bank and pipet 0.5–2 parts (preferably 25 mL) from the transfusion bag into a 1 liter centrifuge bottle.

Add 6–12 parts (preferably 200 mL) 0.2 to 0.6% propionic acid lyse (preferably 0.3%; Cd039–040. It is preferable to reduce the volume of lyse relative to the volume of Source Leukocytes when using the 1 liter process versus the 15 mL process.

After 0.5–3 minutes (preferably 1.5 minutes), and 1–3 parts (preferably 25 mL) of a carbonate buffered quench.

After exposure to the quench for 0.5–6 minutes (preferably 1 minute), centrifuge at 3,000 RPM for 1–3 minutes (preferably 1 minute).

Aspirate the supernatant and replace with a 0.1 to 5% glutaraldehyde solution (preferably 1%) containing 30–80% Ringers (preferably 60%) with 5–20% propylene glycol (preferably 10% propylene glycol) or without propylene glycol. One can obtain qualitatively different populations with and without propylene glycol. The salt concentration in the fix solution is inversely related to the size (volume) of the particles within the 30–80% range of M-Ringers concentration. The change in salt concentration is sensitive to at least a difference of 10% M-Ringers (e.g. 44% Ringers versus 54% Ringers).

Fix for 2 or more hours at room temperature.

An additional fixation may be applied at 10% by volume of reagent glutaraldehyde or formaldehyde to improve cell stability. This is a direct addition of cross-linking agent. Removal of the supernatant and replacement with salt free-fixative will cause a significant change (i.e. drop in volume) of all preserved human white cells.

Wash the cells 1–3 times with M-Ringers. Number of washes depends on the concentration of the residual material, i.e. glutaraldehyde.

Example 4

Saponin only lyse system with one fixation step, no heating, with or without propylene glycol.

Resuspend the Source Leukocyte cells contained in the transfer bags supplied by the blood bank and pipet 0.5–2 parts (preferably 20 mL) from the transfusion bag into a 1 liter centrifuge bottle.

Add 6–12 parts (preferably 200 mL) of saponin solution at 0.2 to 1.625 mL liquid saponin concentrate per liter of working solution (preferably 1.125 ml/L).

The pH of the Source Leukocyte/lyse solution is 6–9 (preferably 6.5–7.5). An acidic environment gives a higher volume and more compact scattergrams than a basic environment.

After 0.5–3 minutes (preferably 2 minutes) for the lysis of the red blood cells, add 1–3 parts (preferably 25 mL) of a salt only (carbonate-free) quench.

After exposure to the quench for 0.5–30 minutes (preferably 1 minute), centrifuge at 3,000 RPM for 1–3 minutes (preferably 1 minute).

Aspirate the supernatant and replace with a 0.1 to 5% glutaraldehyde solution (preferably 1 %) containing 30–80% Ringers (preferably 60%). The salt concentration in the fix solution is inversely related to the size (volume) of the particles within the 30–80% range of concentration. The change in salt concentration is sensitive to at least a difference of about 10% M-Ringers (approximately 10–30 mOsmol).

Fix for 2 or more hours at room temperature. For better stability and appearance, heat for 1–120 minutes at 37° C. (preferably 60 minutes) prior to room temperature fixation. The fixation solution may be added at room temperature or it may be preheated to 37° C.

Wash the cells 1–3 times with M-Ringers. The number of washes depends on the concentration of the residual material, i.e. glutaraldehyde. In general the glutaraldehyde dilution should be $1 \times 10^5$ or preferably $1 \times 10^6$.

Example 5

Resuspend the Source Leukocyte cells contained in the transfer bags supplied by the blood bank and pipet 0.5–2 parts (preferably 20 mL) from the transfusion bag into a 1 liter centrifuge bottle.

Add 6–12 parts (preferably 200 mL) of saponin solution at 0.2 to 1.625 mL liquid saponin concentrate per liter of working lyse solution (preferably 1.125 ml/L). Increasing the saponin concentration will increase the volume of the particles. Increasing the volume of the saponin working solution will increase the volume of the particles. However, excess saponin concentration or an excess quantity of lyse solution will incrementally destroy lymphocytes, monocytes, basophils and eosinophils then finally the neutrophil particles, which are the least sensitive to the saponin treatment.

The pH of the Source Leukocyte/lyse solution is 6–9 (preferably 6.5–7.5). An acidic environment gives a higher volume and more compact scattergrams than a basic environment.

After 0.5–3 minutes (preferably 2 minute) for the lysis of the red blood cells, add 1–3 parts (preferably 25 mL) of a salt only (carbonate-free) quench containing sufficient glutaraldehyde for a final lyse/quench solution containing 0.1–0.3% glutaraldehyde (preferably 0.2% glutaraldehyde).

After exposure to the quench for 0.5–120 minutes (preferably 60 minutes), centrifuge at 3,000 RPM for 1–5 minutes (preferably 1 minute).

Aspirate the supernatant and replace with a 0.1 to 5% glutaraldehyde solution (preferably 1%) containing 30–80% Ringers (preferably 50%) or 30–80% α-napthol-saline solution (preferably 50%). The salt concentration in the fix solution is inversely related to the size (volume) of the particles within the 30–80% range of concentration. The change in salt concentration is sensitive to at least a difference of about 10% M-Ringers (approximately 10–30 mOsmol).

Fix for 2 hours to eight days at room temperature (preferably 3 days). For better stability and appearance, heat for 1–120 minutes at 37° C. (preferably 60 minutes) prior to room temperature fixation. The fixation solution may be added at room temperature or it may be preheated to 37° C.

Wash the cells 1–3 times with M-Ringers. The number of washes depends on the concentration of the residual material, i.e. glutaraldehyde. In general the glutaraldehyde dilution should be $1 \times 10^5$ or preferably $1 \times 10^6$.

Example 6

Saponin only lyse system with three fixation steps with heating.

Resuspend the Source Leukocyte cells contained in the transfer bags supplied by the blood bank and pipet 0.5–2 parts (preferably 20 mL) from the transfusion bag into a 1 liter centrifuge bottle.

Add 6–12 parts (preferably 200 mL) of saponin solution with the final concentration of 0.2 to 1.625 mL liquid saponin concentrate per liter of working solution (preferably 1.125 ml/L). Increasing the saponin concentration will increase the volume of the particles. Increasing the volume of the saponin working solution will increase the volume of the particles. However, excess saponin concentration or an excess quantity of lyse solution will incrementally destroy lymphocytes, monocytes, basophils and eosinophils then finally the neutrophil particles, which are the least sensitive to the saponin treatment.

The pH of the Source Leukocyte/lyse solution is 6–9 (preferably 6.5–7.5). An acidic environment gives a higher volume and more compact scattergrams than a basic environment.

After 0.5–3 minutes (preferably 2 minute) for the lysis of the red blood cells, add 1–3 parts (preferably 25 mL) of a salt only (carbonate-free) quench
  containing sufficient glutaraldehyde for a final lyse/quench solution containing 0.1–0.3% glutaraldehyde (preferably 0.2% glutaraldehyde; ref Cd147; book #21).
  Preferred Method: adding reagent glutaraldehyde directly to the cell/lyse/quench solution to a final concentration of 0.1–0.3% glutaraldehyde (preferably 0.2%) after 1–60 minutes (preferably 5 minutes). Adding reagent glutaraldehyde directly to the cell/lyse/quench is preferred over adding the glutaraldehyde to the quench prior to adding the quench to the lysed Source Leukocyte suspension.

After exposure to the quench for 0.5–120 minutes (preferably 60 minutes), centrifuge at 3,000 RPM for 1–5 minutes (preferably 1 minute).

Aspirate the supernatant and replace with a 0.1 to 5% glutaraldehyde solution (preferably 1%) containing 30–80% Ringers (preferably 50%) or 25–80% α-napthol-saline solution (preferably 50%; ref Cd107, Cd108). The fixation solution may be added at room temperature or it may be preheated to 37° C. The salt concentration in the fix solution is inversely related to the size (volume) of the particles within the 30–80% range of concentration. The change in salt concentration is sensitive to at least a difference of about 10% M-Ringers (approximately 10–30 mOsmol).

Fix for 2 hours to eight days at room temperature (preferably 3 days). For better stability and appearance, heat for 1–120 minutes at 37° C. (preferably 60 minutes) prior to room temperature fixation.

Add aldehyde to 10%–50% of the volume of fixed cells (preferably 10% by volume of glutaraldehyde or formaldehyde).

Fix for 1–5 days (preferably 3 days).

Wash the cells 1–3 times with M-Ringers. The number of washes depends on the concentration of the residual material, i.e. glutaraldehyde. In general the glutaraldehyde dilution should be $1 \times 10^5$ or preferably $1 \times 10^6$.

Example 7

Saponin only lyse system with two fixation steps and no heating:

Resuspend the Source Leukocyte cells contained in the transfer bags supplied by the blood bank and pour 20–60 mL (preferably 40 mL) from the transfer bag into a 1 liter centrifuge bottle. A similar volume may also be obtained from a pooled volume (containing more than one unit) of Source Leukocytes. It is preferable to pool units of Source Leukocytes from blood type compatible units such as combining type "O" and type "A". This reduces the chance of blood cell agglutination.

Add 100–400 mL saponin working solution (preferably 200 mL containing 0.1 mL reagent saponin) and mix for about 1 minute with gentle shaking then set at room temperature for 0.25 to 5 minutes, preferably 2 minutes.

Increasing the volume of the saponin working solution will increase the volume of the particles. However, excess saponin concentration or an excess quantity of lyse solution will incrementally destroy lymphocytes, monocytes, basophils and eosinophils then finally the neutrophil particles, which are the least sensitive to the saponin treatment in this invention.

After 0.25–5 minutes (preferably 2 minutes) for the lysis of the red blood cells in the saponin solution, add 30–80 mL (preferably 60 mL) of a quench, preferably salt only (carbonate-free) with or without cross-linking agent. Mix gently.

The time of quench is 5–90 minutes; preferably 15 minutes.

Using quench with cross-linking agent (e.g. 0.5%–10%; preferably 1% glutaraldehyde by volume of commercial reagent glutaraldehyde; final concentration of 0.25 mL/100 mL), the final volume of the neutrophil population will be lower with increasing volume of quench/cross-linking agent. Increasing the glutaraldehyde to 2% in 50 ML of quench will result in a higher neutrophil volume. Increasing the glutaraldehyde to 10% in quench will result in a lower neutrophil volume. This phenomenon of increased cell volume with a small increase in cross-linking was noted with alligator red cell volume with a small increase in cross-linking was noted with alligator red cells in a prior invention (Carver, Lapicola, and Granier, U.S. Pat. No. 6,146,901). There appears to be an optimal concentration of glutaraldehyde that will result in a maximum cell volume, irrespective of cell type or cell source (e.g. red or white blood cell, human or reptile) using cells that have not been previously exposed to cross-linking agent. A decrease or increase in glutaraldehyde from the optimal will result in a lower cell volume.

After exposure to the quench with or without cross-linking agent, centrifuge at 3,000 RPM for 3–6 minutes, preferably 4 minutes.

Aspirate the supernatant and replace with a 1–20% glutaraldehyde solution (preferably 5%) containing 30–80% Ringers (preferably 50%) or 25–80% α-Napthol-saline solution (preferably 50%). Mix vigorously for about 1 minute.

Fix 1–3 days, preferably 24 hours at room temperature.

Aspirate the supernatant from the gravity settled fixed cells, and add about 100–200 mL of Ringers and suspend by hand shaking.

Add the suspended cells to suspended cells from other bottles until the final volume in the IL bottle is about 500 mL.

Centrifuge at 3,000 RPM for 4 minutes, aspirate supernatant, add 1 volume (i.e. about 500 mL) fresh Ringers and repeat washing step.

Aspirate supernatant and resuspend in a physiological solution that is compatible with the suspending media used to prepare the blood control product.

The present invention provides a simple composition and method for using the composition to provide a hematology blood control product that can be used on a variety of different instruments. The present invention allows the user to customize a process using the method disclosed herein, resulting in a hematology control unique to a hematology instrument specification. There is no need to employ plasma cholesterol in the control of the present invention, thereby reducing its expense and cost. The method and control disclosed herein is simple to use and inexpensive to prepare.

It is apparent from the foregoing that this invention is well-adapted to obtain all the ends and objectives set forth above along with other advantages which are obvious to the invention. It is to be understood that certain features and subcombinations are useful and may be employed without reference to other features and subcombinations. This is contemplated by the disclosure and is within the scope of the claims. Because many possible embodiments may be made with the present invention without departing from its scope, it is further understood that all matters set forth herein are to be interpreted as illustrative only, and no in a limiting sense.

The following is claimed:

1. A hematology control comprising:
    a plurality of leukocytes which have been prepared by
       a) treating the leukocytes with a lytic agent; followed by
       b) treating said leukocytes with a quench; and lastly
       c) treating said leukocytes with at least two post-lytic fixing reagents.

2. The hematology control of claim 1 wherein the lytic agent is an organic acid.

3. The hematology control of claim 2 wherein the lytic agent is selected form the group consisting of formic acid, acidic acid and propionic acid.

4. The hematology control of claim 3 wherein the lytic agent is propionic acid.

5. The hematology control of claim 4 wherein said leukocytes have additionally been treated with a quantity of saponin in step a).

6. The hematology control of claim 5 wherein the saponin is sapindus.

7. The hematology control of claim 1 wherein a third post-lytic fixing reagent is applied to said leukocytes after applying said at least two post-lytic fixing reagents.

8. The hematology control of claim 1 wherein at least one of the post-lytic fixing reagents includes propylene glycol.

9. A method of preparing a hematology control of preserved white blood cells comprising:
    providing a plurality of leukocytes;
    applying a quantity of a lytic reagent to the leukocytes;
    applying a quantity of quench to the leukocytes; and
    applying at least two post-lytic fixing reagents to the leukocytes.

10. The method of claim 9 further comprising the step of adding a third post-lytic fixing reagent to the leukocytes.

11. The method of claim 9 wherein at least one of said post-lytic fixing reagents is applied simultaneously with said quench.

12. A hematology control comprising:
    a plurality of leukocytes which have been prepared by
       a) treating the leukocytes with a lytic agent; followed by
       b) treating said leukocytes with a quench; and lastly, c) treating said leukocytes with at least one post-lytic fixing reagent, wherein steps a), b) and c) are performed sequentially in the order listed, and wherein said leukocytes have additionally been treated with a quantity of sapindus in step a).

13. A hematology control comprising:
a plurality of leukocytes which have been prepared by
   a) treating the leukocytes with a lytic agent; followed by
   b) treating said leukocytes with a quench; and lastly,
   c) treating said leukocytes with at least one post-lytic fixing reagent, wherein steps a), b) and c) are performed sequentially in the order listed, and wherein the post-lytic fixing reagent includes propylene glycol.

14. A method of preparing a hematology control of preserved white blood cells comprising:
   a) providing a plurality of leukocytes;
   b) applying a quantity of lytic reagent to the leukocytes;
   c) applying a quantity of quench to the leukocytes;
   d) applying at least one post-lytic fixing reagent to the leukocytes; and
   e) adding a cross-linking agent to the leukocytes, wherein steps a), b), c), d) and e) are performed sequentially in the order listed.

15. The method of claim 14 further comprising the step of applying a subsequent fixation procedure to the leukocytes after adding said cross-linking agent to the leukocytes.

* * * * *